US006299856B1

(12) United States Patent
DeVore et al.

(10) Patent No.: US 6,299,856 B1
(45) Date of Patent: Oct. 9, 2001

(54) COLLAGEN-BASED DELIVERY OF RADIOACTIVITY FOR USE IN BRACHYTHERAPY

(75) Inventors: Dale P. DeVore, Chelmsford, MA (US); Joel D. Magerman, Blue Bell, PA (US)

(73) Assignee: Collagenesis, Inc., Beverly, MA (US)

( * ) Notice: Subject to any disclaimer, the term of this patent is extended or adjusted under 35 U.S.C. 154(b) by 0 days.

(21) Appl. No.: 09/497,568

(22) Filed: Feb. 3, 2000

Related U.S. Application Data

(60) Provisional application No. 60/119,000, filed on Feb. 8, 1999.

(51) Int. Cl.[7] ............................. A61K 51/00; A61M 36/14
(52) U.S. Cl. ....................... 424/1.69; 424/1.11; 424/1.65; 424/9.1
(58) Field of Search .................................... 424/1.1, 1.65, 424/1.69, 9.1; 530/356

(56) References Cited

U.S. PATENT DOCUMENTS 5,380,646 * 1/1995 Knight et al. ................ 424/1.69
5,418,222 * 5/1995 Song et al. ..................... 514/21

OTHER PUBLICATIONS

Adolfson et al., "Iodine–125 Brachytherapy for clinically localized prostate cancer: A 5–year follow–up of outcome and complications," *Eur. Urol.* 26:207–211 (1994).
Baidoo et al., "$^{99m}$Tc labeling of proteins: Initial evaluation of a novel diaminedithiol bifunctional chelating agent," *Cancer Research* 50:799s–800s (1990).
Chen et al., "A bifunctional ligand for Pd(II)," *Nucl. Med. Biol.* 13:369–372 (1986).
Conway et al., "Palladium (II)–catalyzed olfein–coupling reactions of kainic acid: Effects of substitution on the isopropenyl group on receptor binding," *J. Med. Chem.* 27:52–56 (1984).

Del Regato et al., "Twenty years follow–up of patients with inoperable cancer of the prostate (stage C) treated by radiotherapy: report of a national cooperative study," *I.J. Radiation Oncology Biol. Physics* 26:197–201 (1993).
Gottesman et al., "Failure of open radioactive $^{125}$iodine implantation to control localized prostate cancer: A study of 41 patients," *J. Urology* 146:1317–1320 (1991).
Kaye et al., "Detailed preliminary analysis of $^{125}$iodine implantation for localized prostate cancer using percutaneous approach," *J. Urology* 168:1020–1025 (1995).
Kiernan et al., "Histochemical demonstaration of unsaturated hydrophilic lipids with palladium chloride," *J. Histochemistry and Cytochemistry* 25:200–205 (1977).
Kumar et al., "Vicryl carrier for I–125 seeds: percutaneous transperineal insertion[1]," *Radiology* 159:276 (1986).
Martsev et al., "Modification of monoclonal and polyclonal IgG with palladium (II) coproporphyrin I: stimulatory and inhibitory functional effects induced by two different methods," *J. Immunological Methods* 186:293–304 (1995).
Peschel et al., "Iodine–125 implants for carcimona of the prostate," *Int. J. Radiat. Oncol. Biol. Phys.* 11:1777–1781 (1985).
Weyrich et al., "Iodine 125 seed implants for prostatic carcinoma," *Urology* 41:122–126 (1993).
Wimmer et al., "The antitumor activity of some palladium(II) complexes with chelating ligands*," *Anticancer Research* 9:791–794 (1989).
Zelefsky et al., "Long–term results of retropubic permanent $^{125}$iodine implantation of the prostate for clinically localized prostatic cancer," *J. of Urology* 158:23–30 (1997).

\* cited by examiner

*Primary Examiner*—Dameron L. Jones
(74) *Attorney, Agent, or Firm*—Clark & Elbing LLP

(57) ABSTRACT

Disclosed herein is a method for treating a malignancy in an animal by introducing into the animal a radioactive isotope, or stable element subsequently made radioactive, covalently linked to a collagen. Also disclosed herein are such radiolabeled collagen compositions.

31 Claims, No Drawings

COLLAGEN-BASED DELIVERY OF RADIOACTIVITY FOR USE IN BRACHYTHERAPY

This application claims benefit of provisional application Ser. No. 60/119,000 filed Feb. 8, 1999.

BACKGROUND OF THE INVENTION

In general, the invention relates to the use of collagen-based systems for delivery of anti-cancer agents and therapies.

Despite many advances in treatments, cancer still remains a major cause of death in aging Americans. For example, prostate cancer remains the second most common cause of cancer-related death among males. In 1995, over 240,000 men were diagnosed with prostate cancer in the United States, and more than 40,000 men lost their lives to this disease. Despite these statistics, the ideal treatment for this disease remains controversial. Common treatment recommendations include surgery, external-beam radiation, and brachytherapy.

Surgery is ideally a one-time procedure that may cure prostate cancer in its early stages and extend life in the later stages. However, surgery requires hospitalization, can produce side effects, including impotence and incontinence, and is expensive and can strain limited health care resources.

Alternatively, radiation therapy uses high-energy rays to kill cancer cells. Radiation therapy can be used to treat prostate cancer that has not spread to distant areas of the body. Like surgery, radiation therapy works best when the cancer is located in a small area and, in early stages of prostate cancer, can be very effective. However, since the rays cannot always be directed perfectly, radiation therapy can damage both cancer cells and healthy surrounding tissue.

A third treatment method for prostate cancer is brachytherapy, which is a form of radiation therapy in which radioactive sources are implanted directly into a malignant tumor. This approach offers the appealing concept of delivering a high dose of radiation to a confined volume while sparing adjacent normal tissue.

SUMMARY OF THE INVENTION

The present invention provides a method for treating a malignancy in an animal by introducing, at or near the site of the malignancy, collagen covalently linked to a radioactive isotope or stable element subsequently activated to become radioactive, in an amount sufficient to inhibit or reverse the malignancy.

In preferred embodiments, the malignancy to be treated is a lymphoma, sarcoma, adenoma, glioma, astrocytoma, neuroma, Schwannoma, epithelioma, or, preferably, a malignancy of the prostate or brain. In addition, the invention is suited for treating a malignancy in a mammal, preferably, a human.

In other preferred embodiments, the covalent linking of the collagen to the radioactive isotope is carried out by derivatizing free amine groups (for example, deprotonated free amine groups) of the collagen with the radioactive isotope, or stable element subsequently activated to become radioactive, preferably, at or above a pH of 9.0. Radioactive isotopes which may be used in the invention include $^{103}$Pd, $^{169}$Yb, $^{198}$Au, $^{192}$Ir, $^{10}$B, or, most preferably, $^{125}$I. In another embodiment, the covalent linking of the collagen to a radioactive isotope is performed by derivatizing carboxylic acid side chains with a radioactive isotope, preferably, by using a carbodiimide coupling agent.

The collagen may be in any form, including soluble, gelatinous, as a fibrillar matrix, powder, or bead, and can have a bioresorption rate that is different from naturally-occurring collagen, for example, a rate that is faster or slower (i.e., able to resist bioresorption). Preferably, the collagen has a bioresorption rate that is similar to the decay rate of the covalently-linked radioactive isotope.

The collagen may be used to deliver radioactivity of any appropriate dose, but preferably is used to deliver a covalently-linked isotope at a dose of 0.1 mCi or greater. The isotope may be a stable element subsequently activated to become radioactive using a neutron source. One preferred method of collagen delivery is by injection, for example, to a site at or near the malignancy. One particularly preferred method of delivery is by geodosimetric injection into the tumor.

In a related aspect, the invention also provides radioactive compositions useful for treating a malignancy in an animal. The compositions include collagen covalently linked to a radioactive isotope or stable element subsequently made radioactive, and preferred isotopes include $^{103}$Pd, $^{169}$Yb, $^{198}$Au, $^{192}$Ir, $^{10}$B, and, most preferably, $^{125}$I. The collagen may be, for example, soluble, gelatinous, a fibrillar matrix, powder, or bead and preferably has a faster or slower bioresorption rate than naturally-occurring collagen (for example, a bioresorption rate similar to the decay rate of the covalently-linked radioactive isotope). In other preferred embodiments, the collagen delivers a radioactive dose of 0.1 mCi or greater and is, preferably, designed as a gelling solution that polymerizes upon introduction into a mammal, for example, a human.

As used herein, by "malignancy" is meant an abnormal growth of any cell type or tissue. The term malignancy includes cell growths that are technically benign but which carry the risk of becoming malignant. This term also includes any cancer, carcinoma, neoplasm, neoplasia, or tumor.

By "at or near the site" is meant introducing the collagen implant of the invention to become as physically close to the malignancy as appropriate. This term shall include direct injection into a malignancy particularly, for example, if the malignancy is a solid tumor or encapsulated malignancy.

By "activating" is meant the exposing of a stable element to a radiation source (e.g., neutron source) such that the element is made radioactive.

By "derivatizing" is meant the conversion of a protein (e.g., collagen) into a derivative form of the protein having at least one free amine group or at least one other available reactive group (e.g., carboxylic or sulfhydryl group), covalently linked to a radioactive moiety.

By "radioactive isotope" is meant a chemical element that has the property of spontaneously emitting energetic particles or rays such as alpha particles, beta particles, or gamma rays.

By "solution" is meant any liquid mixture or suspension.

By "gelling solution" is meant any liquid mixture or suspension that has the ability to become a semi-solid gel either ex vivo or in vivo under appropriate conditions.

By "fiber" is meant any semi-solid or solid form of a material that includes fibrils.

By "covalently linked to a collagen" is meant that the radioactive isotope is joined to the collagen either directly through a covalent bond or indirectly through another covalently bonded moiety.

The present invention provides a number of advantages. For example, the methods described herein facilitate treatment of a human patient with a permanent bioresorbable implant for a malignancy that may be difficult to completely or effectively treat by surgery, external beam radiation, chemotherapy, or other means. In addition, these methods may be used in lieu of, or as an adjunct to, more conventional procedures to insure success in inhibiting or reversing malignancies. Because collagen can be bioresorbed, the invention also provides an ideal delivery matrix for chemotherapeutic radioactive isotopes. This feature of the invention allows the radioactive dose to be introduced close to, or within, a malignancy (or the site of a malignancy which has been removed by surgery) which may otherwise be difficult to treat. In addition, radiologic collagen implants can be introduced into a patient permanently and in a minimally invasive way using a hypodermic needle or trocar, thereby eliminating the need for more invasive surgery.

In yet another advantage, according to certain embodiments of the invention, health care workers can introduce a "cold" or non-radioactive implant into a patient and then, post-operatively (and behind protective shielding not possible during a surgical procedure), activate the radioactivity of the patient's collagen implant using an external neutron source. This approach minimizes the radioactive dose to the health care practitioner, providing an important safety advantage.

Other features and advantages of the invention will be apparent from the following detailed description and from the claims.

DETAILED DESCRIPTION OF THE INVENTION

The invention described herein features methods and compositions for treating a malignancy in a mammal using brachytherapy and radiolabeled collagen. As described in more detail below, such radiolabeled collagen was tested in vivo and found to perform as an ideal brachytherapy implant. In addition, different forms of collagen were tested for radiolabeling efficiency and found to be suitable for delivering a radiologic dose sufficient for treating a malignancy. The following examples, which describe these preferred techniques and experimental results, are provided for the purpose of illustrating the invention, and should not be construed as limiting.

EXAMPLE 1

Methods for Preparing and Testing Radiolabeled Collagen for Use In Vivo

To prepare radiolabeled collagen, a collagen fiber dispersion was generated from rabbit dermal tissue using techniques described in U.S. Pat. No. 4,969,912. Dispersions of collagen at 50 mg/ml were suspended in a carbonate buffer at pH 8.5 and covalently iodinated with $^{125}$I using N-Succinimidyl 4-[$^{125}$I] Iodobenzoate (as supplied by Dupont NEN®). The iodination reaction was purposely conducted under suboptimal conditions to limit the specific activity of the collagen implant to be tested in the animal model. Iodination at pH 9.5 can greatly increase the extent of iodination (by fully deprotonating amines). By adjusting labeling conditions in this manner, the radioisotope delivery dose of the collagen implant may be controlled. After radiolabeling of the collagen implant, unbound radiolabel was removed by washing the collagen pellet. Aliquots of radiolabeled collagen (0.5 cc) were then injected submucos-ally into the anterior bladder wall of test animals using a 25-gauge hypodermic needle.

Dosage counts ranged from 19,223 counts per minute (cpm) to 43,856 cpm. Radioactivity was monitored by examining the animals under a gamma camera (Ohio Nuclear Gamma 600) for two minute time periods. Monitoring was done post-operatively, at day one, and then at weekly intervals for up to 56 days. The thyroid, feces, and urine of the test animals were monitored for radioactivity. The decay of $^{125}$I was assayed by recording the counts per minute (CPM) over the area corresponding to the $^{125}$I-radiolabeled collagen implant.

During the first two weeks, test animals exhibited small amounts of radioactivity in the feces and urine. This radioactivity was attributed to residual, unbound $^{125}$I not removed during the three washes of the initial implant preparation. No further collateral radioactivity was noted in the feces or urine of the test animals after 30 days, and there was no radioactivity noted in the thyroid at any time. The radiolabeled collagen implant was easily observed under the gamma camera during the evaluation period. Loss of radioactivity in the bladder wall implant was nearly identical to free-solution $^{125}$I controls indicating the completeness of the covalent labeling achieved.

At postmortem, the collagen implants were easily identified and determined to have retained their initial size and shape. For this demonstration, the collagen fiber dispersion was prepared to retain its structural integrity during this time period. However, collagen preparations that are bioresorbed during the 60-day period can also be prepared (see Example 3). Throughout the 60-day trial, the implants were routinely monitored with a gamma camera, and radioactivity was recorded for up to 50 days. Radioactivity was always concentrated in the implant during the 50-day period, and only minimal extra implant radioactivity was observed, as described above. These results indicated that $^{125}$I-radiolabeled collagen implants were useful for brachytherapy techniques.

EXAMPLE 2

Methods for Determining Dose and Composition of a Radiolabeled Collagen Implant

To prepare a collagen implant having the appropriate dose and composition, the nature of the malignancy to be treated and the degree of bioresorption desired at the treatment site are preferably considered. These factors guide the selection of an appropriate isotope, collagen physical form, and collagen bioresorption rate.

To evaluate the malignancy to be treated, standard techniques (e.g., biopsy, ultrasound, or MRI) may be utilized to determine, for example, cell cycle time, malignancy size, invasiveness, degree of dysplasia, mitotic index, degree of metastasis, and presence of markers indicating cancer phenotype. In addition, other factors such as the overall health of the patient and location of, and access to, the malignancy, contribute to a determination of the suitability of a brachytherapy approach.

This evaluation of the malignancy guides the properties of the radiolabeled collagen implant. For example, the physical form of the implant (e.g., liquid, gel, solid, bead, or powder) may be selected based on this evaluation. In one particular example, if the cancer is well encapsulated, a solution form of collagen implant may be appropriate to insure radiologic intercalation throughout the mass. For this type of malignancy, inappropriate diffusion at the tumor site may be of lesser importance. By contrast, if the malignancy is diffuse, oddly shaped, or adjacent to healthy tissues, an implant that gels upon introduction to the site is preferably selected. Alternatively, a solid implant may also be appropriate. Implants that polymerize or are solid can be introduced into the tumor field in a more controlled manner. In addition, solid implants can be custom molded preoperatively to fit a specific malignancy site or cavity left by a resected tumor.

Finally, each different form of collagen may be further manipulated to have a desirable bioresorption rate. Bioresorption rates of 1 minute to more than 6 months can be achieved. Collagen implants that completely resist bioresorption may also be produced. Bioresorption rates that correlate with the decay rate of the isotope linked to the collagen may be desirable. Such an implant would dissolve at the end of radiotherapy.

With an evaluation of the malignancy, a dosimetry calculation can also be made to aid the selection of an appropriate radioactive isotope. As a guideline, the current dose used in many cancer treatments is 0.45–0.65 mCi of $^{125}$I. However, other dose ranges and isotopes (e.g., $^{103}$Pd, $^{169}$Yb, $^{198}$Au, $^{10}$B, and $^{192}$Ir ) can also be selected.

Several additional calculations may also be utilized in calculating radioactivity delivery doses. For example, $^{125}$I-PIB is typically available at 2200 Ci/mM (Dupont NEN®). Using Avogadro's number, this calculates to 2.2 $\mu$Ci/$10^{11}$ molecules. Molecular collagen contains about 40 NH$_3$+sites per molecule at pH 9.0. Thus, 40 molecules of $^{125}$I will react per collagen molecule resulting in about 8.8×$10^{10}$ $\mu$Ci per molecule of collagen. In 5 mg of collagen/ml this would provide 6.8×$10^{18}$ molecules of $^{125}$I or nearly 150 Ci of $^{125}$I. This dose level for radiolabeled collagen is more than sufficient to be useful in brachytherapy. It should also be noted that several variables sometimes reduce this overall level of activity, including the starting activity of the $^{125}$I, the collagen concentration, the molecular form of the collagen, the reaction efficiency, the number of free NH$_3$+actually available (which is itself dependent on pH), and the competitive reaction of $^{125}$I-PIB.

Thus, it is sometimes desirable to determine the actual activity achievable for a given collagen implant. To make such a determination, the following procedure may be followed. A sample of desired collagen (e.g., acid-soluble collagen, pepsin-digested bovine collagen, dispersed bovine tissue, or neutralized, acid-soluble bovine collagen (EDTA dialysis)) is prepared and labeled with the appropriate isotope (e.g., $^{125}$I-PIB using instructions from Dupont NEN®). The collagen implant material is then dialyzed or washed extensively until the dialysate or wash solution contains near zero radioactivity. An actual aliquot of the implant material is then analyzed for (a) activity (dpm) and Ci/concentration (using standard techniques), (b) ability to polymerize (for example, to undergo fibrillogenesis upon dialysis against PBS at pH 7.2–7.6), and (c) molecular character (for example, using SDS-PAGE or other biochemical tests). Using this procedure, the actual activity for a given radiolabeled sample may be determined.

In addition, although $^{125}$I represents a preferred isotope for chemotherapeutic use, a variety of other isotopes exist for clinical use and may be used in the invention, each isotope having a characteristic energy emission and half-life. These characteristics, as well as the decision of whether to use a temporary or permanent radiolabeled collagen implant, influence the choice of isotope. In addition, the nature of the malignancy, surgical accessibility to the malignancy, the health of the patient, and the patient's ability to withstand different types of surgical procedures and levels of radiation may also be considered in making an isotope selection.

For prostate cancer, $^{125}$I radiolabeled collagen can be supplied as a permanent implant for brachytherapy treatment. This isotope has relatively low energy (27 keV) and a relatively long half-life of 60 days. For other malignancies, other isotopes may be utilized, including $^{103}$Pd (Palladium) with a photon energy of 21 keV and a half-life of 17 days, $^{198}$Au (Gold) with a photon energy of 1.2 MeV and a half-life of only 2.8 days, $^{169}$Yb (Ytterbium) with a photon energy of 93 keV and a half-life of 32 days, and $^{192}$Ir with a photon energy of 400 keV and a half-life of 72 days. High energy isotopes such as $^{192}$Ir and $^{198}$Au are particularly useful when producing temporary collagen implants.

In addition, because the radiation of higher energy sources, such as iridium 192 ($^{192}$Ir) and gold 198 ($^{198}$Au), penetrates further into the tissue, the position of individual sources is less critical to the achievement of a homogeneous dose. However, the greater depth of radiation penetration can result in damage to surrounding normal tissue, potentially causing complications or limiting the actual dose that can be delivered safely to the malignancy.

The radiation of low to moderate energy sources, such as iodine 125 ($^{125}$I), palladium 103 ($^{103}$Pd), and ytterbium 169 ($^{169}$Yb), delivers a more confined dose to the malignancy, but must be placed with precision to avoid areas of under dosage (cold spots) due to the limited penetration of these radiation sources.

The use of boron $^{10}$B has the advantage of being available as a stable, non-radioactive element that can be covalently linked to collagen and subsequently made radioactive. For example, boron can be made into a radioactive, alpha-emitting isotope by exposing to a neutron source, such as a 3 Amp neutron delivery system. Thus, non-radioactive boron-conjugated collagen can be safely introduced into the tumor and then activated externally to become a radioactive implant using a neutron source. Such an implant will then begin to delivery alpha energy to destroy nearby malignant cells.

The initial dose rate of a given isotope is dependent on its half-life and the total dose prescribed. Dose rate is an important determinant of the biological effectiveness of the emitted radiation. For a given unit of radiation, a high dose rate will result in greater biological damage to both normal and malignant tissue than will a low dose rate. Because normal tissue tolerance is the limiting factor for radiation dose, higher dose rate sources are usually prescribed at a lower total dose to avoid complications. Because the relationship between dose rate and cell cycle time of a malignancy is thought to have significance for tumor control, this factor is also preferably considered in the design of a radiolabeled collagen implant.

EXAMPLE 3

Methods for Preparing Different Forms of Radiolabeled Collagen

One advantage to the use of collagen as a delivery vehicle for brachytherapy is the availability of a variety of collagen forms, each having different physical characteristics and bioresorption rates. To test the efficacy of particular forms of collagen, three different collagen preparations having different physical characteristics were analyzed for labeling efficiency and subsequent use in brachytherapy. Sample A was a soluble collagen designed to rapidly polymerize, sample B was a reconstituted collagen solution, and Sample C was a dispersed form of collagen.

Sample A, the rapidly polymerizing collagen solution, was prepared as described in U.S. Pat. No. 5,492,135 (column 14, lines 6–24), except that 35 mM EDTA, disodium salt was used in place of 50 mM EDTA, disodium salt, dialysis was conducted at 4° C., dialysis was continued until the pH was brought to 8.5, and there was no dialysis against deionized water. The final collagen concentration was about 5 mg/ml in the dialyzed preparation.

Sample B, the reconstituted, pepsin-digested bovine collagen solution, was prepared using methods described in U.S. Pat. No. 5,492,135 (column 13, lines 10–64), U.S. Pat. No. 5,631,243 (column 6, lines 63–68 through column 7, lines 1–25), and U.S. Pat. No. 5,210,764 (column 7 through column 8, line 2, except that a centrifugation speed of 9,000 rpm was utilized).

Sample C, the dispersed bovine hide matrix (i.e., fibrillar form of collagen) was prepared using the current "Autologen" process as described in U.S. Pat. Nos. 4,969,912 and 5,067,961.

Radiolabeling of the samples was carried out using N-Succinimidyl 4-[$^{125}$I] Iodobenzoate ($^{125}$I-PIB), and the instructions of the supplier Dupont NEN®. The $^{125}$I-PIB reagent was either used as supplied by the manufacturer or the acetonitrile solvent was allowed to evaporate. Typically, collagen samples were prepared as 5 mg/ml buffered solutions at pH 8.5, and exposed to a 10 μl aliquot of $^{125}$I-PIB preparation for 10 minutes at room temperature with frequent agitation. Iodination was performed using 500 μCi of $^{125}$I-PIB diluted with 20 mM phosphate buffer, pH 8.5, to 120 μl. The highest radiochemical yields were achieved using borate or carbonate buffers at pH 8.5–9.5. When using a weak or small-volume buffer, compensation for the 26 mM acid present in the $^{125}$I-PIB reagent was made by adding at least an equivalent amount of base with or after protein addition such that premature hydrolysis of $^{125}$I-PIB was avoided. Buffers containing thiols or primary amines (glycine or TRIS) were avoided because thiols and amines reacted with the $^{125}$I-PIB reagent and limited labeling yields.

Next, the collagen preparations were distributed as 0.5 cc samples into 1.5 cc microfuge tubes. Three replicates were prepared for each collagen sample. After the 10 minute labeling reaction, Sample A was carefully transferred into dialysis tubing (5,000–6,000 MW cutoff) and placed in 50 ml centrifuge tubes containing 35 mM EDTA, disodium salt, at pH 7.2. The tubes were placed on a rotator at a slow speed. Dialyzing solution was replaced at daily intervals for 1 week and then at weekly intervals. Aliquots were taken for measuring CPMs. Dialyzed $^{125}$I-radiolabeled collagen was also counted at regular intervals.

Samples B and C were centrifuged for 5 minutes in a Biofuge at high speed to separate the fibrous pellet from the clear solution. The solutions were collected and saved for counting. Fresh 4 mM phosphate buffer, pH 7.2, was added to each tube. The tubes were shaken vigorously to disperse the collagen pellet. The tubes were centrifuged, as above, to separate the wash solution from the pellet. This process was repeated several times. Each time, the solution was saved for counting. The pellet, after each wash, was counted using a hand counter. After 120 days the pellet was washed, and the resultant wash solutions and washed pellets were counted.

The results from these radiolabeling experiments are shown in Table 1. Dosimetric evaluation was conducted by measuring the gamma radioactivity at various distances surrounding the $^{125}$I-radiolabeled collagen after 120 days. This time point (120 days) represents the elapse of two half lives when using the isotope $^{125}$I($t_{1/2}$=59.6 d). Results showed a uniform release of activity and expected reduction in activity dependent on the distance from the $^{125}$I-radiolabeled collagen source.

TABLE 1

Radiolabeling Efficiency of a Soluble (Sample A), Reconstituted (Sample B), and Dispersed Collagen (Sample C)

| Sample | TOTAL DPM | μCi Remaining | % Remaining[a] | Adjusted % Remaining[b] |
|---|---|---|---|---|
| A1 | 2,932,730.00 | 1.321 | 13.9 | 11.3 |
| A2 | 3,518,968.00 | 1.585 | 16.7 | 13.5 |
| A3 | 2,720,092.00 | 1.225 | 12.9 | 10.4 |
| Avg.; ± S.E. | 3,057,259 ± 413,764 | 1.377± 0.186 | 14.5 ± 1.97 | 11.73± 1.60 |
| B1 | 3,543,164.00 | 1.596 | 16.8 | 13.6 |
| B2 | 3,431,057.00 | 1.546 | 16.3 | 13.2 |
| B3 | 4,735,294.00 | 2.133 | 22.5 | 18.2 |
| Avg.; ± S.E. | 3,903,164 ± 722,846 | 1.758± 0.325 | 18.53± 3.44 | 15.0 ± 2.78 |
| C1 | 3,102,960.00 | 1.398 | 14.8 | 11.9 |
| C2 | 3,716,443.00 | 1.674 | 17.7 | 14.3 |
| C3 | 1,259,245.00 | 0.567 | 6 | 5.8 |
| Avg.;± S.E. | 2,692,879 ± 1,278,902 | 1.204± 0.566 | 12.83± 6.09 | 10.67± 4.38 |
| CONTROL[a] | 21,026,763.00 | 9.472 | 100 | 100 |

[a]= Compared to the average of two controls, one of which was low due to removal of aliquots for counting at each wash step.
[b]= Based on a single, uncompromised control with an activity of 11.736 μCi remaining.

TABLE 2

Specific Activity ($^{125}$I) of Different Collagen Samples at Day 120

| Sample | μCi$^{125}$I/Sample | μCi$^{125}$I/mg Collagen | mg collagen needed for total 0.5 mCi dose |
|---|---|---|---|
| Sample A (soluble) | 11.7 | 4.7 | 106.4 |
| Sample B (reconstituted) | 15.0 | 6.0 | 83.3 |
| Sample C (dispersed) | 10.7 | 4.3 | 116.3 |

As shown in the above tables, sample B was the collagen form most efficiently labeled. About 15% of the $^{125}$I radiolabel remained incorporated in the sample B collagen implant after 120 days. Collagen forms represented by samples A and C were labeled with essentially the same efficiency and retained approximately 11% of the input label after 120 days (Table 1). This was partly due to the reduced number of free amine sites that were available for derivatizing in samples A and C. Importantly, however, all implant forms (samples A–C) retained over 10% of the incorporated isotope (after preliminary washes) over the time period tested (120 days) (Table 1).

These labeling experiments also allowed for dose calculations, and these are summarized in Table 2. For example, sample A was prepared to an activity of 4.7 μCi per mg of collagen. At this activity, administering a dose of 0.5 mCi (500 μCi) would require 106 mg of soluble $^{125}$I-radiolabeled collagen. Since base solutions can be prepared at a concentration of up to 50 mg/ml, only a little more than 2 cc of injectate is necessary to deliver a brachytherapy dose of 0.5 mCi.

Sample B, composed of reconstituted bovine collagen, would require about 83 mg of collagen to deliver a dose of 0.5 mCi. This form of reconstituted bovine collagen can be prepared to a concentration of about 50 mg/ml. Again, a minimal injectate volume (less than 2 cc) can be used to provide a sufficient radiologic dose to treat a malignancy.

Sample C, composed of dispersed bovine dermis, would require about 116 mg of collagen to deliver a dose of 0.5 mCi of $^{125}$I activity. This is because sample C was composed of fibrillar collagen with fewer binding sites for derivatizing with $^{125}$I-PIB. Thus, sample C must be prepared at a relatively high collagen concentration (about 200 mg/dose) in order to provide an effective radiologic dose.

These doses are calculated for day 120. To deliver a similar dose at day zero, four fold less collagen would be required. Thus, at a concentration of 50 mg/ml, as little as 500 μl of one of the above collagens would be needed to deliver 0.5 mCi of radioactivity. Accordingly, to deliver 0.1 mCi of radioactivity, only a fifth of the above dosage is required.

Results from these labeling experiments demonstrated that collagen could be derivatized with $^{125}$I to provide a radiologic dose comparable to current dosages (e.g., 0.45–0.65 mCi per dose) used to treat a range of malignancies. In addition, sample A rapidly forms a gelatinous/fibrous mass when exposed to physiological liquid or tissue fluids. As a result, this material can be used in applications that require a space filling capability followed by rapid polymerization to avoid subsequent diffusion, for example, the radiologic sterilization of a tumor site in the brain following surgical resection.

Finally, both collagen implants A and B may be conveniently injected through a 27 to 30 gauge needle. Upon injection, sample A instantly becomes gelatinous or fibrous, whereas sample B undergoes some spontaneous aggregation. It is believed that sample A, the rapidly polymerizing soluble collagen, will be an ideal form for delivering radioactivity to a tumor due to its ease of injection and its ability to form an intact gel at the injection site. Sample B appeared to migrate into tissue surrounding the injection site. In addition, both samples A and B can be molded ex vivo into desirable implant shapes for implanting into a malignancy site. Additional methods for introducing radiolabeled collagen implants into an animal are provided in Example 4.

EXAMPLE 4

Methods for Using Radiolabeled Collagen for Brachytherapy

A variety of brachytherapy approaches are available for treating malignancies. Methods of implantation involve either temporary implants, where the radioisotopes are left in the patient for a calculated time and then removed, or permanent implants, where the radioisotopes are permanently implanted into the patient and allowed to decay to an inert state over a predictable time. Temporary implants are often combined with external-beam radiation therapy, while permanent implants are generally used alone. The methods of the invention are ideally suited for providing either a permanent or temporary implant using minimally invasive methods.

The methods of the invention allow for a permanent radiolabeled collagen implant to be introduced into the patient using a needle or trocar (a sharp-pointed instrument equipped with a cannula). Placement of the implant can be guided by high-resolution ultrasound or computer tomography.

Ideally, methods are utilized to intraoperatively visualize the needle or trocar insertion into the site of the malignancy. This real-time visualization affords enhanced accuracy of implant placement within the site of the malignancy and allows for the identification and correction of potential sources of error, such as movement of the malignancy and internal tissue distortion that may occur during needle or trocar insertion. This improved imaging ability and use of a needle or trocar obviates the need for a surgical incision, permitting this procedure to be done on a cost-effective outpatient basis.

In addition, patient morbidity can be further reduced by forgoing the use of a trocar and instead using a thin-walled 17- or 18-gauge needle that penetrates the tissue with minimal trauma. Software is available that incorporates ultrasound signal units to accurately display coordinates superimposed over real-time images of the malignancy, providing targets for the accurate placement of needles into the malignancy field. These techniques can also be used to monitor the polymerization of a radiolabeled collagen and further insure that sufficient radiolabeled collagen has been introduced and placed in an optimal location for inhibiting or reversing the malignancy.

In treating a malignancy of the prostate the above considerations generally apply in addition to the following guidance. First, clinicians typically conduct a preoperative study using ultrasound or computer tomography to accurately determine the exact volume and contour of the malignancy. Second, sophisticated, treatment-planning computer programs are used to customize dose distributions based on measurements of the target volume. For the computer analysis, the contours of the prostate target volume, bladder neck, and rectum are entered into a computer program so that needle entry and source strengths can be considered.

Three-dimensional dose distributions of radiation are calculated for the prostate, rectum, and bladder, and variables can be adjusted to optimize the dose to the prostate and minimize the dose to adjacent tissue. This method facilitates the creation of an idealized implant, customized to account for the wide range of individual prostate sizes and shapes. In addition, the ability to introduce a liquid radiolabeled collagen implant that is space filling and capable of polymerizing and retaining a defined shape at the tumor site is an advantage of this approach.

While these methods are ideal for the treatment of malignancies of the prostate, the methods also allow for the treatment of a number of other malignancies. For example, an important advantage of the invention is the ability to treat brain malignancies (e.g., gliomas, neuromas, and astrocytomas) that are difficult to effectively or completely treat with surgery. For example, even if a malignancy of the brain is surgically removed, radiosterilization of the tumor site may be required. If the brain tumor surgically resected is of significant size, the surgeon may also need an implant with space filling properties to reoccupy the tumor site. The methods of the invention provide an ideal implant that satisfies all of these demands.

Finally, the present method provides radiolabeled collagen implants that can be designed to resist bioresorption and thus serve as ideal temporary implant material for the treatment of any malignancy. The implant can be fashioned into a solid form, molded into any shape to fit the tumor site, and after implantation, be readily distinguished from other tissues for easy recovery. A temporary radiolabeled collagen implant may be especially desirable if treatment of the malignancy calls for the use of a high energy source (e.g., $^{192}$Ir) that needs to be applied for only hours or days.

OTHER EMBODIMENTS

The invention described herein provides a method for inhibiting or reversing a malignancy in an animal by introducing into the animal a collagen implant covalently linked to a radioactive isotope. Such an implant may include any form of collagen and any appropriate radioisotope (e.g., $^{103}$Pd, $^{169}$Yb, $^{198}$Au, $^{192}$Ir, $^{125}$I, or $^{10}$B). The radioisotope is covalently linked to the collagen by standard techniques. As demonstrated herein, collagen can be covalently linked to $^{125}$I by reacting deprotonated collagen with N-succinimidyl 4-($^{125}$I) Iodobenzoate (DuPont NEN). In another example, covalent bonding of $^{103}$Pd to collagen is accomplished by conjugating carboxylic acid side chains of collagen using a carbodiimide coupling agent following the formation of a stable complex of $^{103}$Pd with 6-(5-carboxyl pentyl)-5, 7 dioxo-1, 4, 8, 11-tetraazaundecane. In yet another example, a stable element such as boron (B) is covalently linked to collagen by standard techniques and subsequently rendered radioactive ($^{10}$B) by exposing to a neutron source.

In addition to the above-described collagen forms, other forms of collagen suitable for brachytherapy applications are powder and bead forms. These forms of collagen are discussed in U.S. Pat. Nos. 4,969,912 and 5,067,961 and methods for their preparation are incorporated by reference herein.

In addition, while the methods described herein are preferably used for the treatment of human patients, non-human animals (e.g., pets and livestock) may also be treated using the methods of the invention.

All publications and patent applications mentioned in this specification are herein incorporated by reference to the same extent as if each independent publication or patent application was specifically and individually indicated to be incorporated by reference.

What is claimed is:

1. A method of treating a malignancy in an animal, said method comprising introducing, at or near the site of said malignancy, collagen covalently linked to a radioactive isotope or stable element subsequently activated to become a radioactive isotope, in an effective amount to inhibit or reverse said malignancy.

2. The method of claim 1, wherein said malignancy is a lymphoma, sarcoma, adenoma, glioma, astrocytoma, neuroma, Schwannoma, or epithelioma.

3. The method of claim 1, wherein said malignancy is a prostate malignancy.

4. The method of claim 1, wherein said malignancy is a brain malignancy.

5. The method of claim 1, wherein said animal is a mammal.

6. The method of claim 5, wherein said mammal is a human.

7. The method of claim 1, wherein said collagen is covalently linked to a radioactive isotope or stable element subsequently activated to become a radioactive isotope by derivatizing free amine groups with a radioactive isotope or stable element.

8. The method of claim 1, wherein said collagen is covalently linked to a radioactive isotope or stable element by derivatizing carboxylic acid side chains with a radioactive isotope or stable element.

9. The method of claim 8, wherein said derivatizing is performed using a carbodiimide coupling agent.

10. The method of claim 7, wherein said derivatizing is performed at or above pH 9.0.

11. The method of claim 7, wherein said radioactive isotope is $^{125}$I, $^{103}$Pd, $^{169}$Yb, $^{198}$Au, $^{192}$Ir, or $^{10}$B.

12. The method of claim 7, wherein said stable element is boron (B).

13. The method of claim 11, wherein said radioactive isotope is $^{125}$I.

14. The method of claim 1, wherein said collagen is soluble, gelatinous, a fibrillar matrix, a powder, or a bead.

15. The method of claim 1, wherein said collagen has a bioresorption rate that is faster than naturally-occurring collagen.

16. The method of claim 1, wherein said collagen resists bioresorption.

17. The method of claim 1, wherein said collagen has a bioresorption rate similar to the decay rate of said covalently linked isotope.

18. The method of claim 1, wherein said isotope is delivered at or greater than about 0.1 mCi.

19. The method of claim 1, wherein said stable element is subsequently activated using a neutron source.

20. The method of claim 1, wherein collagen is introduced at or near said malignancy by injection.

21. A composition comprising collagen covalently linked to a radioactive isotope or a stable element which is subsequently activated to become a radioactive isotope.

22. The composition of claim 21, wherein said radioactive isotope is $^{125}$I, $^{103}$Pd, $^{169}$Yb, $^{198}$Au, $^{192}$Ir, or $^{10}$B.

23. The composition of claim 21, wherein said stable element is boron (B).

24. The composition of claim 21, wherein said radioactive isotope is $^{125}$I.

25. The composition of claim 21, wherein said stable element is subsequently activated using a neutron source.

26. The composition of claim 21, wherein said collagen is soluble, gelatinous, a fibrillar matrix, a powder, or a bead.

27. The composition of claim 21, wherein said collagen has a bioresorption rate that is faster than naturally-occurring collagen.

28. The composition of claim 21, wherein said collagen resists bioresorption.

29. The composition of claim 21, wherein said isotope is delivered at or greater than about 0.1 mCi.

30. The composition of claim 21, wherein said collagen is a gelling solution that polymerizes upon introduction into a mammal.

31. The composition of claim 21, wherein said collagen has a bioresorption rate between 1 minute and 6 months.

* * * * *